(12) United States Patent  
Haddad

(10) Patent No.: US 9,314,193 B2  
(45) Date of Patent: Apr. 19, 2016

(54) BIOMETRIC APPARATUS AND METHOD FOR TOUCH-SENSITIVE DEVICES

(71) Applicant: Biogy, Inc., San Francisco, CA (US)

(72) Inventor: Waleed Sami Haddad, San Francisco, CA (US)

(73) Assignee: BIOGY, INC., San Francisco, CA (US)

( * ) Notice: Subject to any disclaimer, the term of this patent is extended or adjusted under 35 U.S.C. 154(b) by 0 days.

(21) Appl. No.: 13/651,408

(22) Filed: Oct. 13, 2012

(65) Prior Publication Data

US 2013/0094719 A1   Apr. 18, 2013

Related U.S. Application Data

(60) Provisional application No. 61/546,838, filed on Oct. 13, 2011, provisional application No. 61/563,138, filed on Nov. 23, 2011.

(51) Int. Cl.
| | |
|---|---|
| G06K 9/00 | (2006.01) |
| A61B 5/117 | (2006.01) |
| H04W 12/06 | (2009.01) |
| H04L 29/06 | (2006.01) |
| A61B 5/00 | (2006.01) |
| G06F 3/01 | (2006.01) |
| G06F 3/041 | (2006.01) |

(52) U.S. Cl.
CPC ............... *A61B 5/117* (2013.01); *A61B 5/6898* (2013.01); *G06F 3/011* (2013.01); *H04L 63/0861* (2013.01); *H04W 12/06* (2013.01); *G06F 3/0414* (2013.01)

(58) Field of Classification Search
CPC .......... G07C 9/00158; G06K 9/00885; G06K 9/0002; G06K 9/00026; G06K 9/00013; G06K 9/00067; G06K 9/00087
USPC ................... 382/115, 124, 126; 361/200, 230
See application file for complete search history.

(56) References Cited

U.S. PATENT DOCUMENTS

| | | | |
|---|---|---|---|
| 5,386,104 | A | 1/1995 | Sime |
| 5,862,246 | A | 1/1999 | Colbert |
| 6,202,151 | B1 | 3/2001 | Musgrave et al. |
| 6,688,891 | B1 | 2/2004 | Sanford |
| 6,895,507 | B1 | 5/2005 | Teppler |

(Continued)

FOREIGN PATENT DOCUMENTS

| | | |
|---|---|---|
| EP | 2323022 | 5/2011 |
| KR | 1020070036277 | 4/2007 |

(Continued)

OTHER PUBLICATIONS

Office Action dated Mar. 24, 2015 from EP Application No. 12840140.3, 8 pages.

*Primary Examiner* — Ruiping Li  
(74) *Attorney, Agent, or Firm* — Hollingsworth Davis, LLC

(57) ABSTRACT

A touch sensor is configured to sense a contact event occurring between a body part of a user and the touch sensor. The touch sensor is configured to produce contact data in response to the sensed contact event. A processor is coupled to the touch sensor and memory. The processor is configured to store in the memory a sequence of data frames each comprising contact data associated with a different portion of the user's body part. The processor is further configured to generate biometric signature data using the sequence of data frames.

23 Claims, 11 Drawing Sheets

(56) References Cited

U.S. PATENT DOCUMENTS

| | | |
|---|---|---|
| 6,898,709 B1 | 5/2005 | Teppler |
| 6,935,951 B2 | 8/2005 | Paulsen et al. |
| 6,948,069 B1 | 9/2005 | Teppler |
| 6,996,538 B2 | 2/2006 | Lucas |
| 7,197,167 B2 | 3/2007 | Chung et al. |
| 7,290,072 B2 | 10/2007 | Quraishi et al. |
| 7,409,557 B2 | 8/2008 | Teppler |
| 7,428,319 B2 | 9/2008 | Bezvershenko et al. |
| 7,451,925 B2 | 11/2008 | Bonalle et al. |
| 7,496,509 B2 | 2/2009 | Navratil et al. |
| 7,596,246 B2 | 9/2009 | Miller et al. |
| 7,606,396 B2 | 10/2009 | Miller et al. |
| 7,630,522 B2 | 12/2009 | Popp et al. |
| 7,657,287 B2 | 2/2010 | Hausner et al. |
| 7,680,263 B2 | 3/2010 | Nice et al. |
| 7,688,314 B2 | 3/2010 | Abdallah et al. |
| 7,704,147 B2 | 4/2010 | Quraishi et al. |
| 7,708,191 B2 | 5/2010 | Vega |
| 7,740,243 B1 | 6/2010 | Kean |
| 7,819,750 B2 | 10/2010 | Lam et al. |
| 7,886,157 B2 | 2/2011 | Beenau et al. |
| 7,894,634 B2 | 2/2011 | Chung |
| 7,898,385 B2 | 3/2011 | Kocher |
| 7,900,259 B2 | 3/2011 | Jeschke et al. |
| 7,995,802 B2 | 8/2011 | Hu et al. |
| 8,033,515 B2 | 10/2011 | Martin et al. |
| 8,063,889 B2 | 11/2011 | Anderson |
| 8,087,988 B2 | 1/2012 | Nguyen et al. |
| 8,141,155 B2 | 3/2012 | Jeschke et al. |
| 8,289,136 B2 | 10/2012 | Beenau et al. |
| 8,412,623 B2 | 4/2013 | Moon et al. |
| 8,468,211 B2 | 6/2013 | Miller |
| 2001/0036297 A1 | 11/2001 | Ikegami et al. |
| 2003/0117281 A1 | 6/2003 | Sriharto et al. |
| 2004/0161728 A1 | 8/2004 | Benevento et al. |
| 2004/0236699 A1 | 11/2004 | Beenau et al. |
| 2005/0206501 A1 | 9/2005 | Farhat |
| 2005/0213799 A1* | 9/2005 | Sawano ................. 382/124 |
| 2006/0016868 A1 | 1/2006 | Bonalle et al. |
| 2006/0203880 A1 | 9/2006 | Batcho |
| 2007/0011463 A1 | 1/2007 | Garfinkle |
| 2007/0048723 A1 | 3/2007 | Brewer et al. |
| 2007/0197261 A1 | 8/2007 | Humbel |
| 2007/0273658 A1 | 11/2007 | Yli-Nokari et al. |
| 2008/0285814 A1 | 11/2008 | Di Carlo et al. |
| 2008/0316045 A1 | 12/2008 | Sriharto et al. |
| 2009/0076875 A1 | 3/2009 | Lert et al. |
| 2009/0082951 A1 | 3/2009 | Graessley |
| 2009/0184932 A1 | 7/2009 | Alten |
| 2009/0265544 A1 | 10/2009 | Moona et al. |
| 2010/0046810 A1* | 2/2010 | Yamada ................. 382/124 |
| 2010/0289772 A1 | 11/2010 | Miller |
| 2011/0002461 A1 | 1/2011 | Erhart et al. |
| 2011/0310044 A1 | 12/2011 | Higuchi |
| 2012/0206586 A1* | 8/2012 | Gardner ................. 348/77 |

FOREIGN PATENT DOCUMENTS

| | | |
|---|---|---|
| KR | 1020110000844 | 1/2011 |
| KR | 1020110108646 | 10/2011 |
| WO | WO2010098094 | 9/2010 |

\* cited by examiner

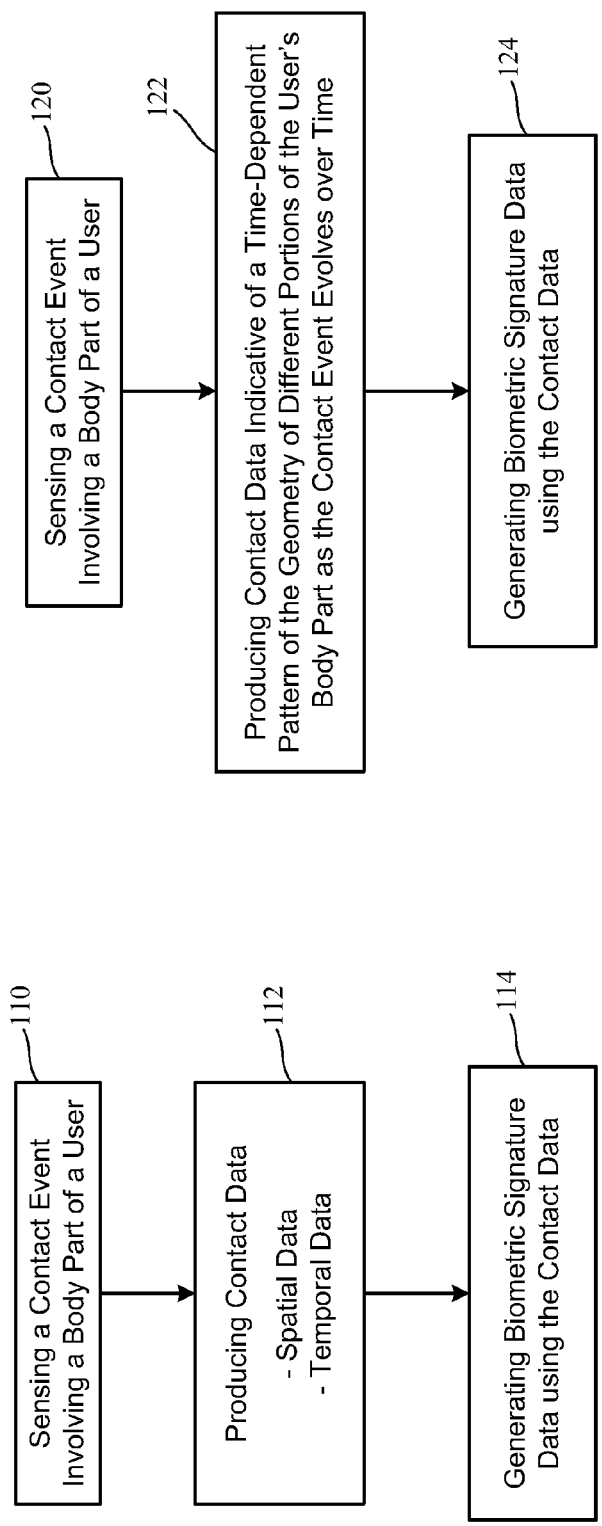

BIOMETRIC APPARATUS AND METHOD FOR TOUCH-SENSITIVE DEVICES

RELATED PATENT DOCUMENTS

This application claims the benefit of Provisional Ser. Nos. 61/546,838, filed on Oct. 13, 2011, and 61/563,138, filed on Nov. 23, 2011, to which priority is claimed pursuant to 35 U.S.C. §119(e) and which are hereby incorporated herein by reference.

SUMMARY

Embodiments of the disclosure are directed to a biometric system and method for use in devices that include a touch sensor. Method embodiments of the disclosure involve sensing a contact event occurring between a body part of a user and a touch sensor and storing, for the contact event, a sequence of data frames each comprising contact data associated with a different portion of the user's body part. Method embodiments further involve generating biometric signature data using the sequence of data frames.

Apparatus embodiments of the disclosure include a touch sensor configured to sense a contact event occurring between a body part of the user and the touch sensor. The touch sensor is configured to produce contact data in response to the sensed contact event. A processor is coupled to the touch sensor and memory. The processor is configured to store in the memory a sequence of data frames each comprising contact data associated with a different portion of the user's body part. The processor is further configured to generate biometric signature data using the sequence of data frames.

These and other features can be understood in view of the following detailed discussion and the accompanying drawings.

BRIEF DESCRIPTION OF THE DRAWINGS

FIGS. 1-5 are flow diagrams showing biometric processes in accordance with various embodiments of the disclosure;

DESCRIPTION

Figure 3:
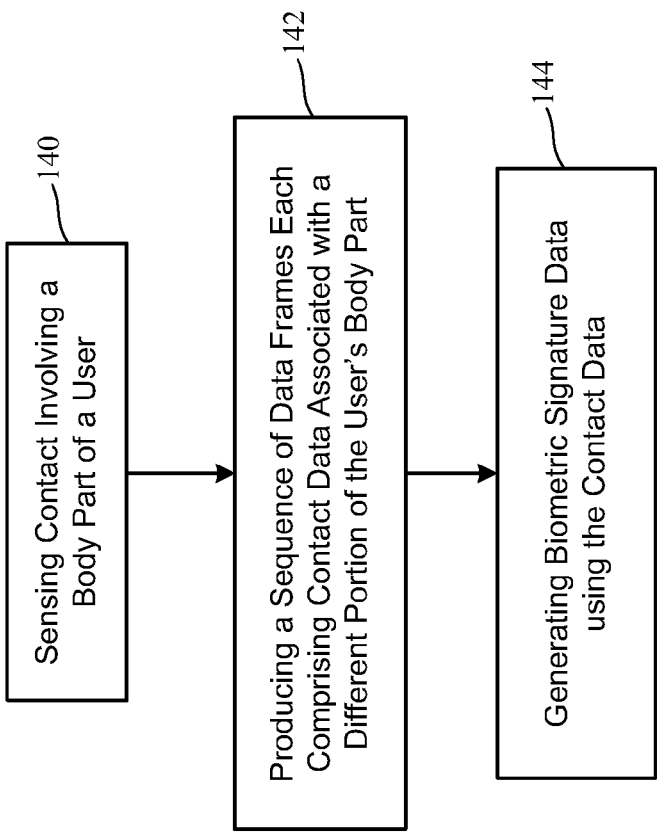

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Embodiments of the disclosure relate to a biometric system and method for use with a wide variety of systems and devices. A biometric system and method according to embodiments of the disclosure find particular utility when incorporated into mobile electronic devices, such as portable communication devices.

In the context of portable communication devices, there is a rapidly increasing need for a biometric system that can be implementable on common, currently available mobile devices, mainly mobile phones and tablet computers. This need appears to be becoming critical as the use of mobile devices for conducting transactions, and in particular financial transactions, increases, while the sophistication, and therefore the risk, of cyber crime grows.

Despite the apparent trajectory for the use of mobile devices, and the obvious advantages of biometrics as a component of an effective security protocol, there is no readily available biometric device that is easily implementable on mobile phones. There are small, inexpensive fingerprint readers (swipe sensors, and a few area sensors) that are appearing on some phone models, as well as a few voice and face recognition applications that can be used with the microphone or camera available on most phones, however these work poorly, and would require additional, or much better biometric hardware to be added to the phone in order for them to be reliable and accurate enough to provide serious security. User acceptance is also a very important factor in biometrics, and many users are wary of the familiar biometric systems, and in particular of fingerprint readers.

A new biometric system that is easy to use, simple to implement using existing hardware on mobile phones and tablets, and is different enough from any of the common biometrics that are used now could fill the need for an effective way of verifying a user's identity without a long technology development cycle, or the need for hardware manufacturers to build a new device into their products. This would allow the added security of biometrics to be put in place on the very short timescale needed to support the rising security needs of mobile transactions.

Embodiments of the inventions described herein use modern touch screen technology to acquire the patterns of one, two, three or four of the user's fingers pressed onto the screen together, or in a particular sequence. To increase the sophistication, and amount of usable biometric information, a time-dependent pattern is used, not just a simple static finger geometry pattern. In other words, a rapid series of "frames" of the user's finger geometry is recorded as he/she presses down onto the screen. Because of the natural 3-D geometry of a user's fingers and hand, this time-dependent pattern has additional and useful complexity. This time-dependence actually allows each user to develop a special technique of hand placement, perhaps with additional conscious movements that only he/she knows, in a sense adding a password-like component to the pattern.

Since the user's hand geometry is unique, and not controlled by the user, there will always be involuntary components to the biometric signature that are unknown, even to the user, both spatially (the hand geometry pattern in 2-D on the screen), as well as the involuntary time dependence (the way the pattern changes over time as the user presses down on the screen). This is critical for biometric security because it cannot be given away, even by the user himself/herself.

The additional possibility that the user can also make extra voluntary movements during hand placement creates even more uniqueness, and therefore valuable complexity to the biometric "signature" that will be used by the system. Furthermore, the approach is not limited to hand or finger geometry. It can be used with other body parts, most notably the pinna of the ear. This can be seen as potentially desirable since most touch screen phones are constructed in such a way that when the user holds the phone to talk, he/she will inevitably press his/her ear against the touch screen somewhat consistently every time the phone is used. It may be possible to successfully enroll the ear print pattern in the same way as the time-dependent hand print pattern would be, and then to use this ear print pattern as another biometric signature. In principle, other body parts could also be used, such as the lips, knuckles, a part of the arms or legs, foot, etc. These are not likely to be as practical as the hand, or even the pinna of the ear, but they are mentioned here for completeness.

One significant advantage of the added element of time-dependence of the biometric signature is that there will not be any possibility for hackers to "lift" a so-called "latent print." Latent prints are a problem with some fingerprint systems because the user may leave a clear image of his/her fingerprint on the sensor (or possibly elsewhere) that can be copied using one of several methods, and used to create a false fingerprint, or, in some cases, the latent print left on a sensor can be induced to trigger the sensor again through the application of heat, cold, illumination, or something else, depending on the sensor technology. The issue of latent prints is essentially rendered inconsequential by the element of time-dependence in the approaches described herein.

This approach is chosen because the resolution of current touch screens is suitable for such use, but they are not capable of resolving finer patterns, such as those of a fingerprint. The use of time dependence in the biometric embodiments disclosed herein represents a unique capability not found in conventional biometrics. The temporal component of the data differentiates it from other biometrics, and opens up a number of possibilities for the user to participate in creating the "password" or "key", as well as for increasing the complexity of the biometric signature.

The spatial dimension of the data will be quite low-resolution with current state-of-the-art touchscreens, and therefore not by itself contain sufficient information, however, with the time dimension added, the dataset will effectively be three-dimensional, and contain a great deal of information that can be used to differentiate a large number of users, as well as provide enough information density to overcome the difficulties of natural variations in biometric signatures from which all biometric systems suffer. If the touchscreen happens to have the ability to also measure pressure as a function of position on the screen, such as a pressure-sensitive touch screen does, then yet another dimension can be added to the biometric signature: that of pressure. The data set would now effectively be four-dimensional, having two spatial dimensions and pressure, all as a function of time.

Turning now to FIG. 1, there is illustrated a flow diagram showing biometric processes in accordance with various embodiments. The biometric method depicted in FIG. 1 involves sensing 110 a contact event involving a body part of a user, and producing 112 contact data. The contact data preferably includes spatial data associated with the 2-D geometry of the user's body part and temporal data associated with the development of a contact pattern for the contact event. The method of FIG. 1 further involves generating 114 biometric signature data using the contact data. It is noted that content of the contact data can be different for different embodiments of the disclosure.

A typical contact event involves an intentional touching of a touch sensitive device by a user. For example, the user may place one or more fingers (or palm, for example) on a touch sensor of the touch sensitive device, which can define a contact event. By way of further example, the user may use one or more fingers to swipe across a region of the touch sensor, which can define a contact event. It is understood that a wide variety of static (stationary) and dynamic (moving) contact events are contemplated. It is noted that, in the case of a static contact event, a resulting contact event still involves development of a contact pattern over time, since the area of contact between the user's body part and the touch sensor changes between initial contact and a stationary state.

FIG. 2 illustrates a flow diagram showing various biometric processes in accordance with other embodiments. In FIG. 2, the biometric method involves sensing 120 a contact event involving a body part of a user, and producing 122 contact data. The contact data preferably includes data indicative of a time-dependent pattern of the geometry of different portions of the user's body part as the contact event evolves over time. The method of FIG. 2 further involves generating 124 biometric signature data using the contact data.

The flow diagram illustrated in FIG. 3 shows various biometric processes in accordance with some embodiments. The biometric method shown in FIG. 3 involves sensing 130 a contact event involving a body part of a user, and producing 132 contact data. The contact data according to this embodiment preferably includes data indicative of a chronology of frames of data of the contact event (referred to herein as "contact data frames"). The method of FIG. 3 further involves generating 134 biometric signature data using the contact data.

Figure 4:
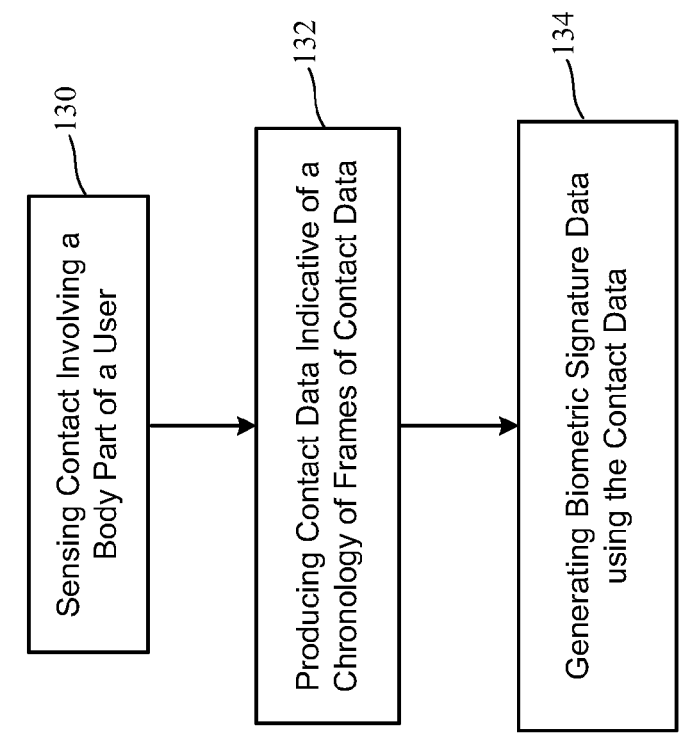

FIG. 4 illustrates a flow diagram showing various biometric processes in accordance with further embodiments. In FIG. 4, the biometric method involves sensing 140 a contact event involving a body part of a user, and producing 142 a sequence of data frames each comprising contact data associated with a different portion of the user's body part as the contact pattern develops. The method of FIG. 4 also involves generating 144 biometric signature data using the contact data.

Figure 5:
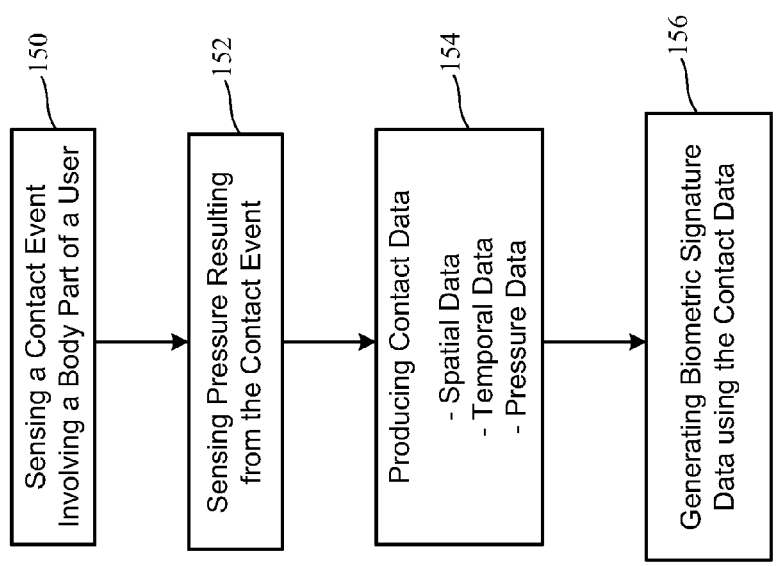

Embodiments of the disclosure can acquire other and/or additional data for purposes of implementing various biometric processes. According to the embodiment shown in FIG. 5, the biometric method involves sensing 150 a contact event involving a body part of a user, and sensing 152 pressure resulting from the contact event. Contact data is produced 154 for this contact event from which a contact pattern can be developed. The contact data in FIG. 5 preferably includes spatial data associated with the 2-D geometry of the user's body part, pressure data associated with the touch, and temporal data associated with the development of a contact and pressure profile for the contact event. The method of FIG. 5 also involves generating 154 biometric signature data using the contact data.

Figure 6:
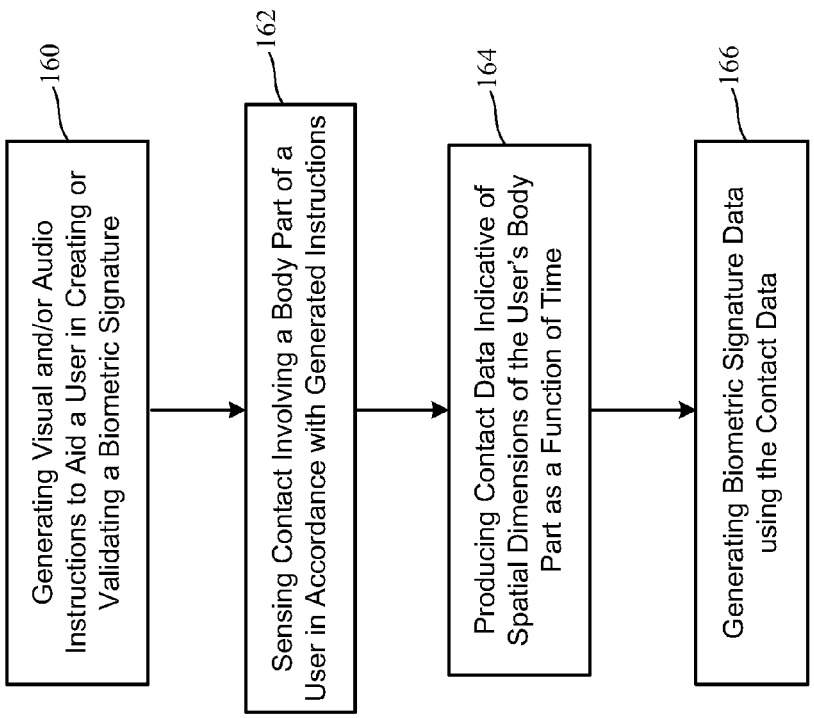
FIG. 6 is a flow diagram showing biometric processes including generation of visual and/or audio instructions in accordance with various embodiments of the disclosure.

FIG. 6 illustrates a flow diagram showing various biometric processes in accordance with some embodiments. In FIG. 6, the biometric method involves generating 160 visual and/or audio instructions to aid a user in creating or validating a biometric signature. The method also involves sensing 162 a contact event involving a body part of a user in accordance with the generated instructions, and producing 164 contact data indicative of spatial dimensions of the user's body part as a function of time. The method of FIG. 6 further involves generating 166 biometric signature data using the contact data.

Figure 7:
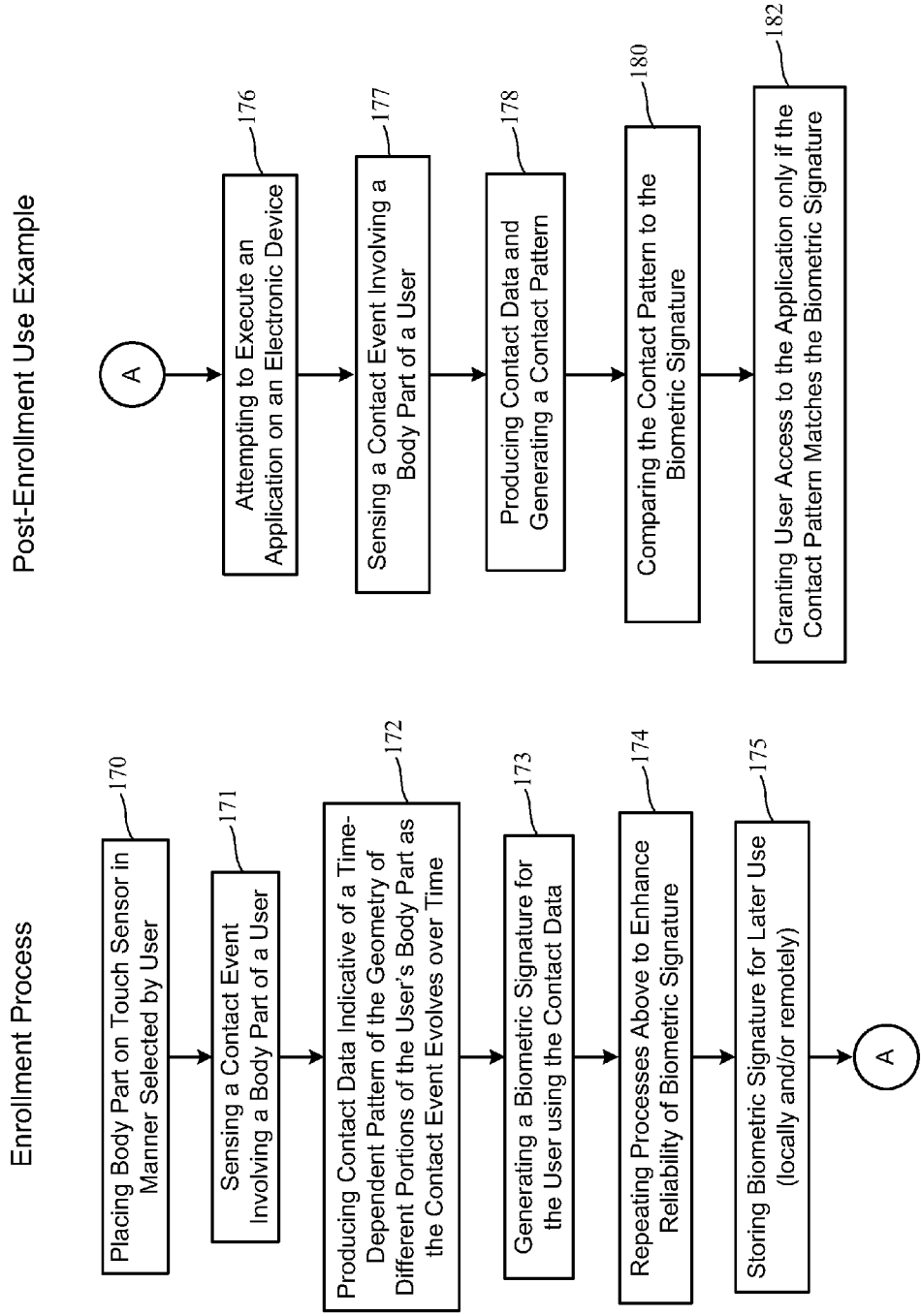
FIG. 7 is a flow diagram showing biometric processes involving an enrollment process for generating a biometric signature and post-generation use of the biometric signature in accordance with various embodiments of the disclosure.

The flow diagram of FIG. 7 illustrates an enrollment process for generating a biometric signature and post-generation use of the biometric signature in accordance with various embodiments of the disclosure. During the enrollment process, a user establishes his or her biometric signature which, once created, can be used to provide secured access to electronic devices, applications, websites, and other secured systems and software processes (e.g., bank transactions via a mobile phone or tablet).

The enrollment process shown in FIG. 7 (blocks 170-175) involves the user placing 170 a body part on a touch sensor. The user may select which body part (e.g., hand or ear) and number of body parts to be used to create the user's biometric signature. For example, the user may choose to use 3 figures that are placed near the center of the touch sensor. In another example, the touch sensor may be pressed against the pinna of the user's ear, which may be convenient for secured use of mobile phones that incorporate a touch sensor.

With the body part being placed on the touch sensor, the enrollment process involves sensing 171 a contact event involving the selected body part(s), and producing 172 contact data. The contact data according to this embodiment preferably includes data indicative of a time-dependent pattern of the geometry of different portions of the user's body part as the contact event evolves over time. The method further involves generating 173 a biometric signature for the user using the contact data. The processes of blocks 170-173 may be repeated 174 to enhance the reliability (e.g., stability, repeatability) of the user's biometric signature. The enrollment process concludes with storing 175 the user's biometric signature for subsequent use. The biometric signature can be stored locally on a mobile electronic device owned by the user, on a remote server or both locally and remotely. The user's biometric signature is now available for use with various secured applications, websites, services, systems, and devices that require user authentication.

In the post-enrollment use example illustrated in FIG. 7 (blocks 176-182), it is assumed that a biometric algorithm of the present disclosure is operating on an electronic device and that the device is operating an application that requires user authentication prior to allowing use or access to the device and/or application. At a time subsequent to the enrollment process, the method of FIG. 7 further involves attempting 176 to execute a secured application on the electronic device, which may be a mobile phone, tablet or PC, for example. Attempting to execute the application involves creating a contact pattern for the user in the same manner as when generating the user's biometric signature. It is understood that the touch sensor and/or electronic device used to generate the biometric signature can be the same as, or different from, those used to produce the contact pattern.

With continued reference to FIG. 7, a touch sensor of the electronic device senses 177 contact with a body part of the user and produces 178 contact data in a manner previously described. The body part(s) brought into contact with the touch sensor of the electronic device is the same as that/those used to create the user's biometric signature. The just-produced contact pattern is compared 180 to the user's biometric signature to authenticate the user. This comparison can be performed by the electronic device, by a remote system communicatively coupled to the electronic device, or cooperatively by both entities. The user is granted access 182 to the application only if the contact pattern matches the biometric signature.

Figure 8:
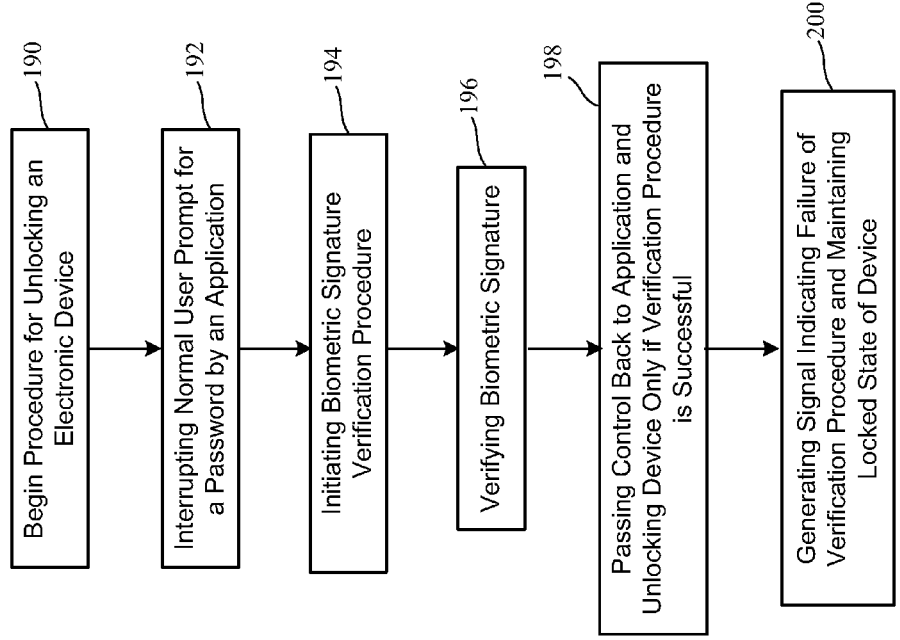
FIG. 8 is a flow diagram showing biometric processes involving unlocking of an electronic device using a biometric signature in accordance with various embodiments of the disclosure.

FIG. 8 illustrates a flow diagram showing various biometric processes in accordance with some embodiments. In FIG. 8, a procedure for unlocking 190 an electronic device is initiated. It is assumed in the illustrative embodiment of FIG. 8 that a biometric algorithm of the present disclosure is operating on the electronic device and that the device is operating an application that requires user authentication prior to allowing use or access to the device and/or application. The unlocking procedure involves interrupting 192 a normal password prompt typically generated by the application. Instead, a biometric signature verification procedure of the present disclosure is initiated 194. Contact data resulting from sensing contact between a user's body part and a touch sensor of the electronic device is acquired, from which a time-dependent contact pattern is generated. This time-dependent contact pattern is used by the biometric algorithm to verify 196 authenticity of the user.

The biometric algorithm passes 198 back control to the application and the electronic device is unlocked only if the verification procedure is successful. If the verification procedure is unsuccessful (i.e., the contact pattern constructed from the contact data does not match the user's biometric signature), a signal indicative of such failure is generated 200, and the electronic device is maintained in the locked state. In response to the generated signal, a message indicating the unsuccessful verification is communicated to the user, typically via a visual and/or audio message.

Figure 9:
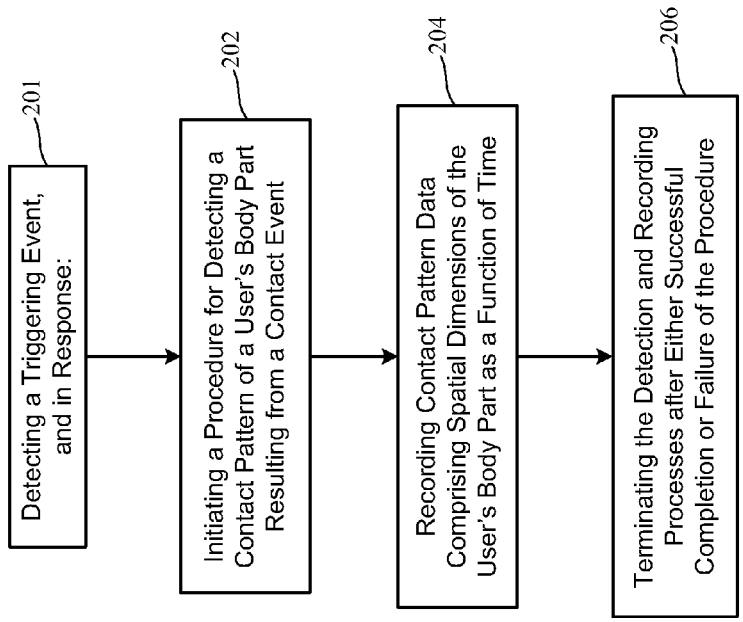
FIGS. 9-11 and 13 are flow diagrams showing biometric processes involving a triggering algorithm in accordance with various embodiments of the disclosure.

In accordance with the biometric processes shown in FIG. 9, various embodiments of the disclosure provide for detection 201 of a triggering event which, when detected, causes initiation of biometric signature data acquisition. Detection 201 of a triggering event causes initiation 202 of a procedure for detecting a contact pattern of a user's body part relative to a touch sensor that results from a contact event with the touch sensor. The method further involves recording 204 contact pattern data comprising spatial dimensions of the user's body part in contact with the touch sensor as a function of time. The method also involves terminating 206 the detection and recording processes after either successful completion or failure of the contact pattern detection procedure. It is understood that a variety of triggering methodologies are contemplated, and that a triggering protocol can be implemented for one or both of the biometric signature and contact pattern generation processes.

The addition of the time dimension adds a complexity that is both desirable, and potentially excessive, however this complexity can be quantized and controlled through creative design of the data acquisition algorithms. The excessive complexity can come from the fact that a user may change the "speed" with which he/she executes the hand placement on the touchscreen, effectively shortening, or lengthening the extent of the dataset in the time dimension depending on if the placement is faster or slower. This would be the case if acquisition of each "frame" of the pattern is acquired according to an independent clock that runs on the device, collecting the data in fixed time steps in the same way a movie camera, for example, acquires a sequence of images of a scene. This can make matching with the enrolled pattern difficult. One way to handle this is to develop algorithms that can compress or stretch the dataset in the time dimension as part of the pattern-matching component of the biometric algorithm suite. Such a method may be based on existing "morphing" techniques, wavelet transforms, or other known methods, or it may be developed specifically for use in this application. This is one viable approach, however, it is not likely to be the fastest or most efficient, and may have other problems.

An alternate, and possibly better approach would be to quantize the time dimension of the data during acquisition based on the pattern itself, and not on an independent clock. This would require specialized triggering algorithms to "step" the acquisition of the pattern on the screen as a function of time while the user is making the placement. Since the only important thing in the time dimension is what aspects of the pattern appear first, second, third, and so on, by quantizing time through special triggering that is based on the fundamental properties of the pattern itself as it develops during the placement, the time axis of the data set will be controlled in real time, during the placement unintentionally by the user him/herself in an automated fashion. The time aspect of the user's hand placement need not be linear in this case, as the triggering algorithm will "examine" the pattern as it develops in time, and trigger the capture of the "movie frames" of the pattern automatically based on some criteria of the image (pattern) itself. There are several possible designs for this specialized triggering algorithm, examples of which are described below.

Figure 10:
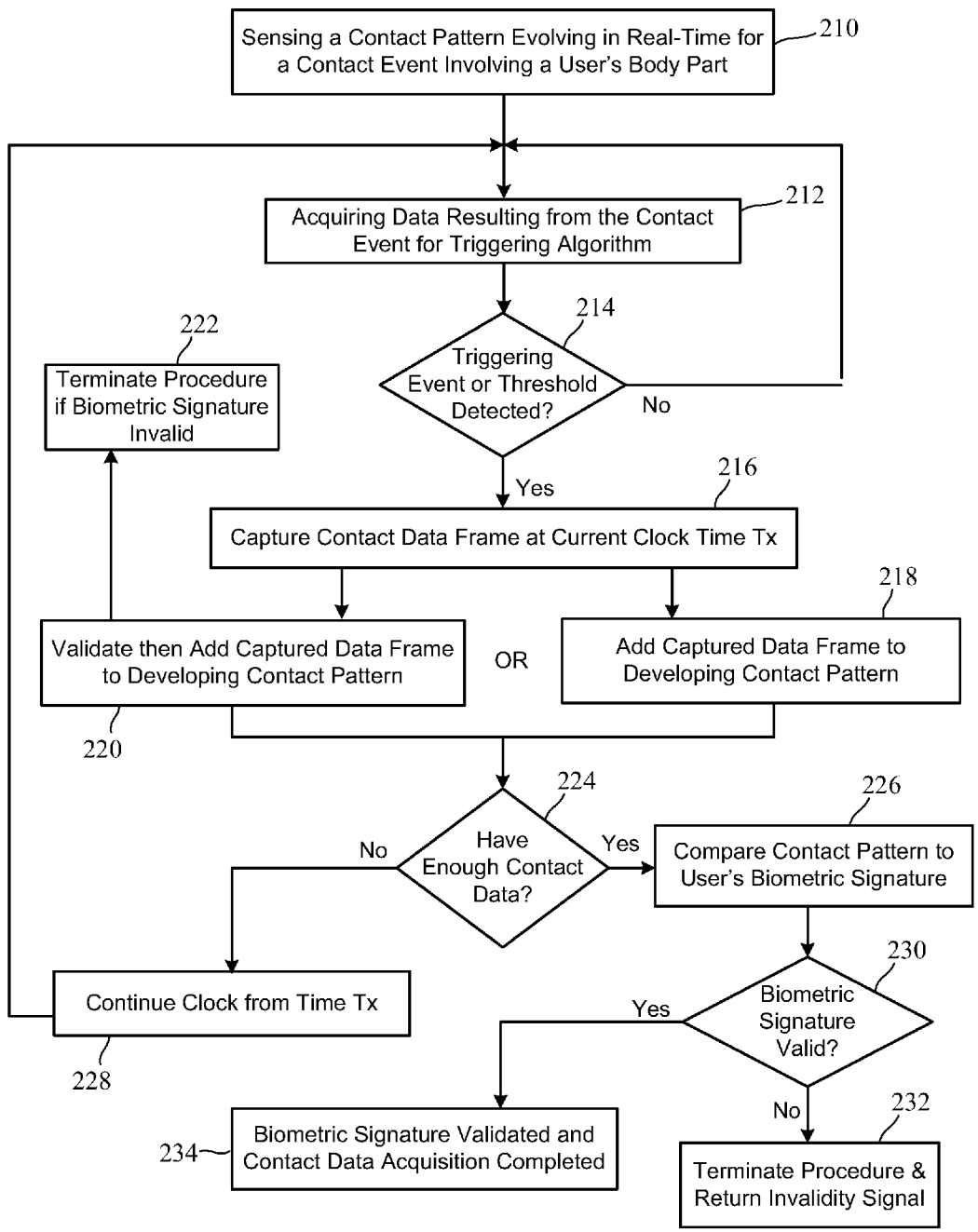

FIG. 10 illustrates a flow diagram showing various biometric processes including a triggering methodology in accordance with various embodiments. FIG. 10 shows a number of different processes involving generating a contact pattern in response to a triggering event and validating this contact pattern against a pre-established biometric signature for the user. In general terms, the triggering processes described herein rely on storing of a sequence of data "points", which are taken during the enrollment process or are predetermined somewhat arbitrarily. During use of a secured electronic device, for example, when the user places his/her hand on the touch sensor (e.g., screen), the thresholds for triggering are based on these stored data points (for example, a series of different total mass count levels as is described below). As the placement occurs, the decision to trigger capturing of a frame of contact data is made based on the first data point (ith data point), then, once that is done, the next triggering event is based on the second data point (ith+1 data point), and so forth. As discussed previously, the triggering and contact data generation methodologies shown in FIG. 10 can be implemented for one or both of the biometric signature and contact pattern generation processes.

The processes shown in FIG. 10 include sensing 210 a contact pattern evolving in real-time for a contact event involving a body part of a user. The method also involves acquiring 212 data from the contact event that is used by a triggering algorithm, which is typically running on an electronic device operable by the user. If the acquired data meets or exceeds a triggering threshold 214, a triggering event is declared and a frame of contact data is captured 216 at a current clock time Tx. If the acquired data fails to meet or exceed the triggering threshold 214, the data acquisition process of block 212 continues.

Each triggering event 214 results in the capturing 216 of an additional frame of contact data for the contact event. Over time, the sequence of captured data frames defines a contact pattern that evolves as the contact event evolves. At some stage of the procedure, a validation operation occurs to verify whether or not the developing or developed contact pattern corresponds to the pre-established biometric signature of the user. In some embodiments, each captured contact data frame is added 218 to a developing contact pattern which, when sufficiently formed, is subsequently subjected to validation. In other embodiments, each captured frame of contact data to be added to a developing contact pattern is subjected to validation 220 against the pre-established biometric signature of the user. By way of example, if a given frame of captured contact data is determined to be out of sequence relative to its expected position within the contact data frame sequence of the biometric signature, this contact data frame would be considered invalid.

As the contact data capturing routine continues, a test 224 is made to determine if enough contact data has been collected for the developing contact pattern. If not, the clock continues to run 228 and the data acquisition process in block 212 continues. If a sufficient amount of contact data has been collected for the developing contact pattern, the contact pattern is compared 226 to the user's pre-established biometric signature. If determined to be invalid, the procedure of FIG. 10 is terminated 232 and an invalidity signal is generated. If determined valid, the procedure of FIG. 10 is terminated 234 and a signal confirming validity is generated. It is understood that the validation processes of blocks 226, 230, and 232 would not be implicated when creating the user's biometric signature in accordance with the methodology shown in FIG. 10.

Verification of a biometric signature can involve a number of different validation techniques. One approach involves comparing a temporal order of data frames of a developing or developed contact pattern to that of the biometric signature. Another approach involves comparing characteristics of the time-dependent spatial data of a contact pattern with those of the biometric signature. It is to be understood that there are many ways to use the contact information collected in space and time, including arranging the 3-D data (2-D in space, and 1-D in time) into a new format of 2-D data that can be tested for verification using existing pattern recognition methods. In fact, the biometric signature can be created from this data in a number of different ways.

According to some embodiments, triggering of screen image capture can be based on "total mass" count (TMC) of the image as a function of time. Triggering can be quantized based on the total amount of "mass" or ratio of bright to dark pixels of the screen that are filled. As the user places his/her hand on the touchscreen, the area filled by the parts of the screen that are covered by the hand is added up to provide a "total mass" count (TMC) as a function of time. This TMC can be based on either a binarized version of the image, or the grayscale version. It may be the case that using the binarized version of the image to calculate the TMC will be more reliable for triggering purposes, but this will depend on the properties of the screen, and the user's hand.

Triggering on the capture of image data of the user's hand during placement will then be set to occur upon reaching specific values of the TMC in sequence as the user places his/her hand on the screen during verification. Thus, triggering of sequential "frames" of the touchscreen image of the user's hand will not depend on the time, but upon the image data itself being captured. The TMC values used for the triggering can be simply arbitrary values from low to high, or a set of other, perhaps non-linearly increasing values of the TMC. The set of TMC triggering values may be determined at the time of enrollment by the user, and can be based on the TMC values reached over a linear time sequence during the enrollment process, after which the originally-used time sequence can be abandoned, and triggering will be based on the predetermined TMC values. Otherwise, any other favorable sequence of TMC values can be predetermined, and used for the triggering process, if such a set of values is known from testing to deliver reliable triggering results over a variety of users.

Figure 11:
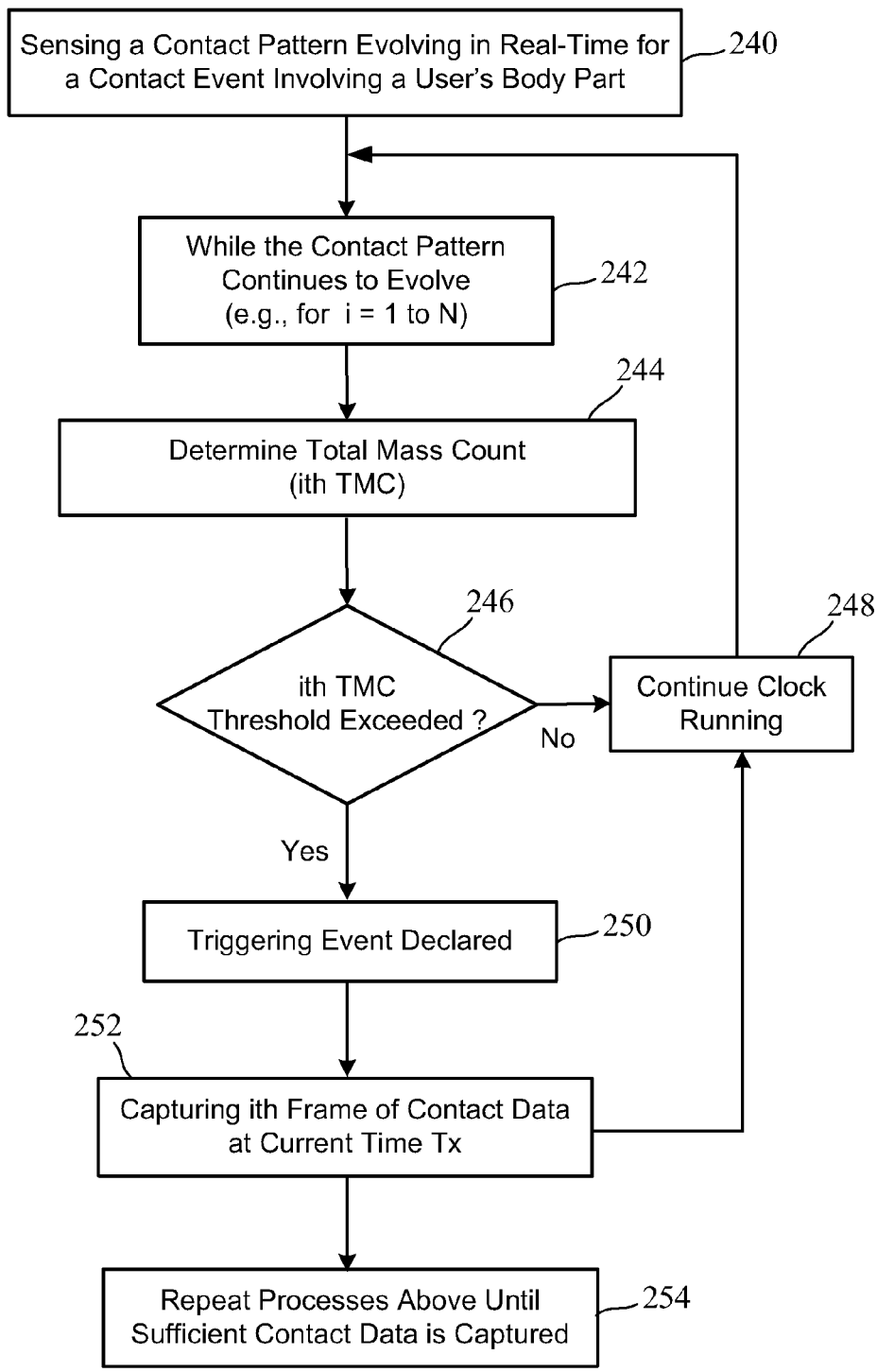
Figure 12:
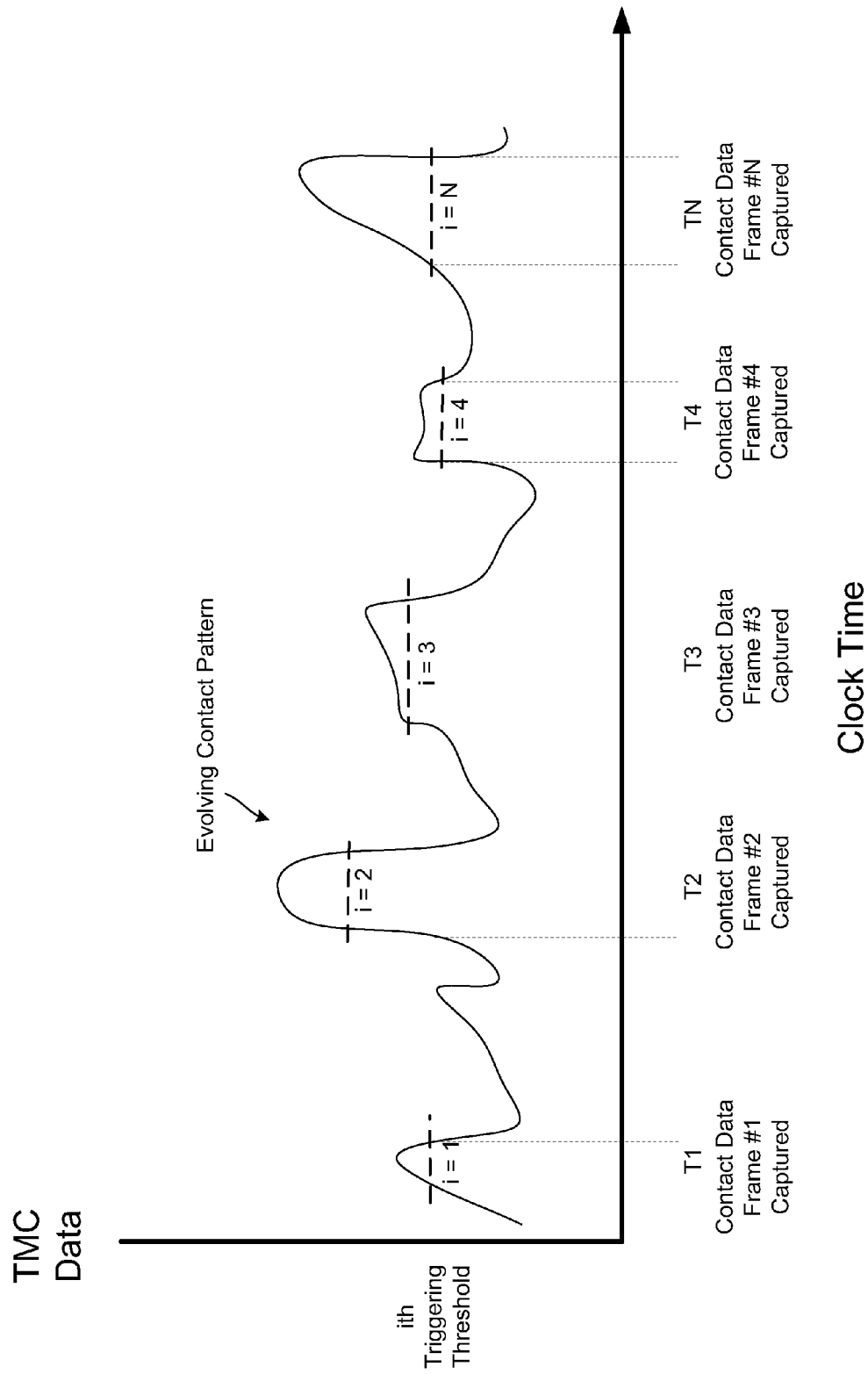
FIGS. 12 and 14 are diagrams depicting aspects of biometric processes involving the triggering algorithms of FIGS. 11 and 13, respectively, in accordance with various embodiments of the disclosure.

FIG. 11 illustrates a flow diagram showing various biometric processes including a triggering methodology in accordance with some embodiments. In FIG. 11, the biometric method involves sensing 240 a contact pattern evolving in real-time for a contact event involving a user's body part. While the contact pattern continues to evolve 242 (e.g., for i=1 to N), the total mass count (ith TMC) of the contact pattern image is determined 244. If the ith TMC exceeds an ith predetermined threshold 246, a triggering event is declared 250, and an ith frame of contact data is captured 252 at the current clock time Tx. If not, the clock continues to run and the processes beginning at block 242 continue. The processes above continue 254 until a sufficient amount of contact data (e.g., i=N) has been captured, at which point a validation process may be initiated. FIG. 12 illustrates an evolving contact pattern relative to predetermined triggering thresholds. When the ith TMC of the contact pattern exceeds the ith triggering threshold, an ith frame of contact data is captured at the current clock time Tx, thereby creating a sequence (i=1 to N) of contact data frames.

According to other embodiments, triggering of screen image capture can be based on sequential filling of spatial regions of the screen. Instead of using TMC to determine the points in time at which each new image frame is captured during the hand placement on the screen, the filling of various regions of the screen can be used as triggering events. This can be done by dividing up the screen area into a number or regions prior to verification. This can be done arbitrarily, for example by dividing the area up on a 2-D grid, with rectangular regions that are equal to, or larger than, the fundamental spatial resolution of the screen, or using any other arbitrary, pre-determined segmentation desired, such as concentric arc-shaped segments, etc. The arbitrary segmentation can be done, and stored in the device memory prior to the use of the application by any user, or prior to its use by each user. It can also be done after enrollment by the user, thereby making the segmentation map unique for each user.

By choosing the shape and size of segments of the screen to examine during later verification attempts based on how the user placed his/her fingers during enrollment, the triggering scheme can be optimized for each user, and for the way each user places his/her fingers on the screen. This would be done via an algorithm that analyzes the finger contact pattern during enrollment, and storing information about the time sequence in which various regions of the screen are "filled" as the user enrolls. The exact time at which a region is filled does not matter, only the relative time at which regions get filled.

During verification, first, a start command would initiate the process, and the device will wait to capture a full screen image until the first triggering region is filled. Once this happens, the device again waits until the next screen region in the sequence is filled, and triggers another full-screen image capture. This process continues until verification is terminated. The termination point can also be triggered either by the filling of all the designated regions, or when the final region in the sequence is filled. It can also be terminated early if the designated regions are filled out of sequence. This can be used as part of the verification process.

A user's verification attempt can be rejected early if the placement fills the regions in a sequence that is too different from the sequence (or sequences, since enrollment will usually require more than one placement for reliability) stored during enrollment. If the user has shifted his/her position up, down, left or right along the screen during verification compared with the original location during enrollment, a simple translation shift can be applied when analyzing the filling of the screen regions in order to compensate for this. A similar sort translation shift must be used when comparing the actual enrollment pattern with any verification pattern as well.

Figure 13:
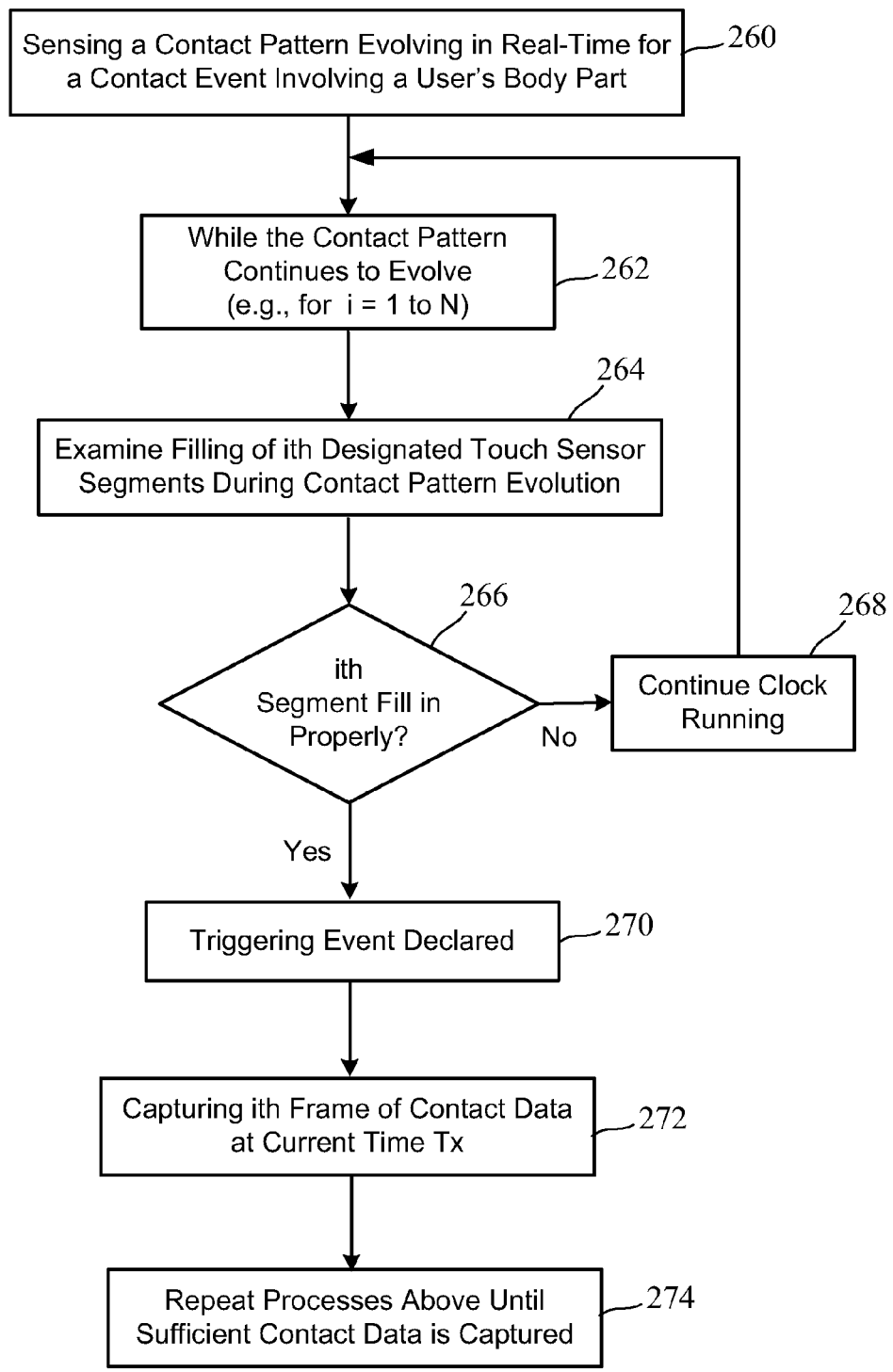
Figure 14:
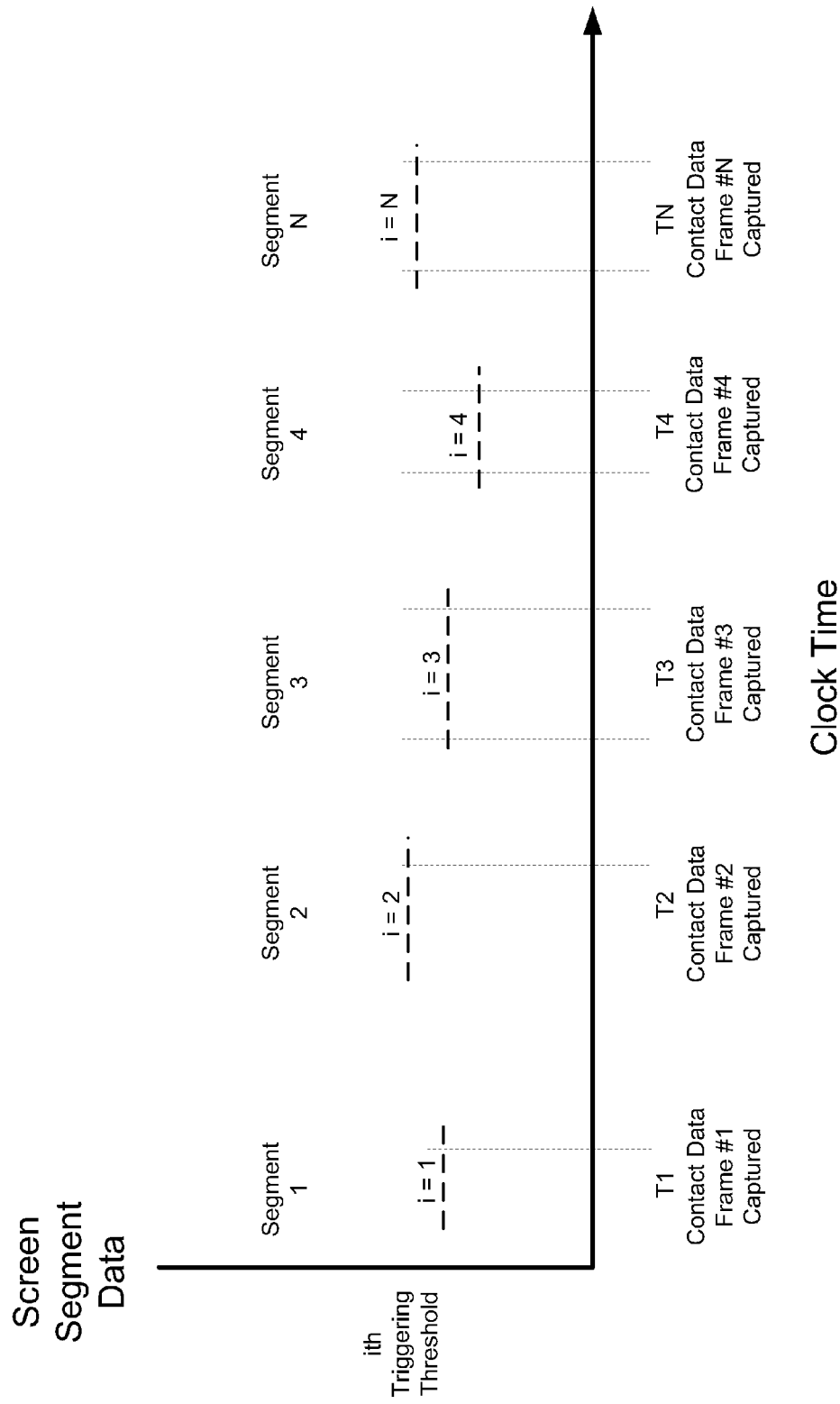

FIG. 13 illustrates a flow diagram showing various biometric processes including a triggering methodology in accordance with some embodiments. In FIG. 13, the biometric method involves sensing 260 a contact pattern evolving in real-time for a contact event involving a user's body part. While the contact pattern continues to evolve 262 (e.g., for i=1+N), the filling of designated touch sensor segments due to being covered by the user's body part is examined 264. A test is made to determine 266 if a current (ith) segment is properly filled relative to an predetermined ith threshold. If not, the clock continues to run 268 and the processes beginning at block 262 continue. If the current segment is properly filled, a triggering event is declared 270 and an ith frame of contact data is captured 272 at the current clock time Tx, thereby creating a sequence of contact data frames. The processes above continue 274 until a sufficient amount of contact data has been captured, at which point a validation process may be initiated. FIG. 14 illustrates an evolving contact pattern relative to a predetermined triggering thresholds. When filling of an ith segment during contact pattern evolution exceeds an ith triggering threshold, an ith frame of contact data is captured at the current clock time Tx, thereby creating a sequence of contact data frames (i=1 to N).

Figure 15:
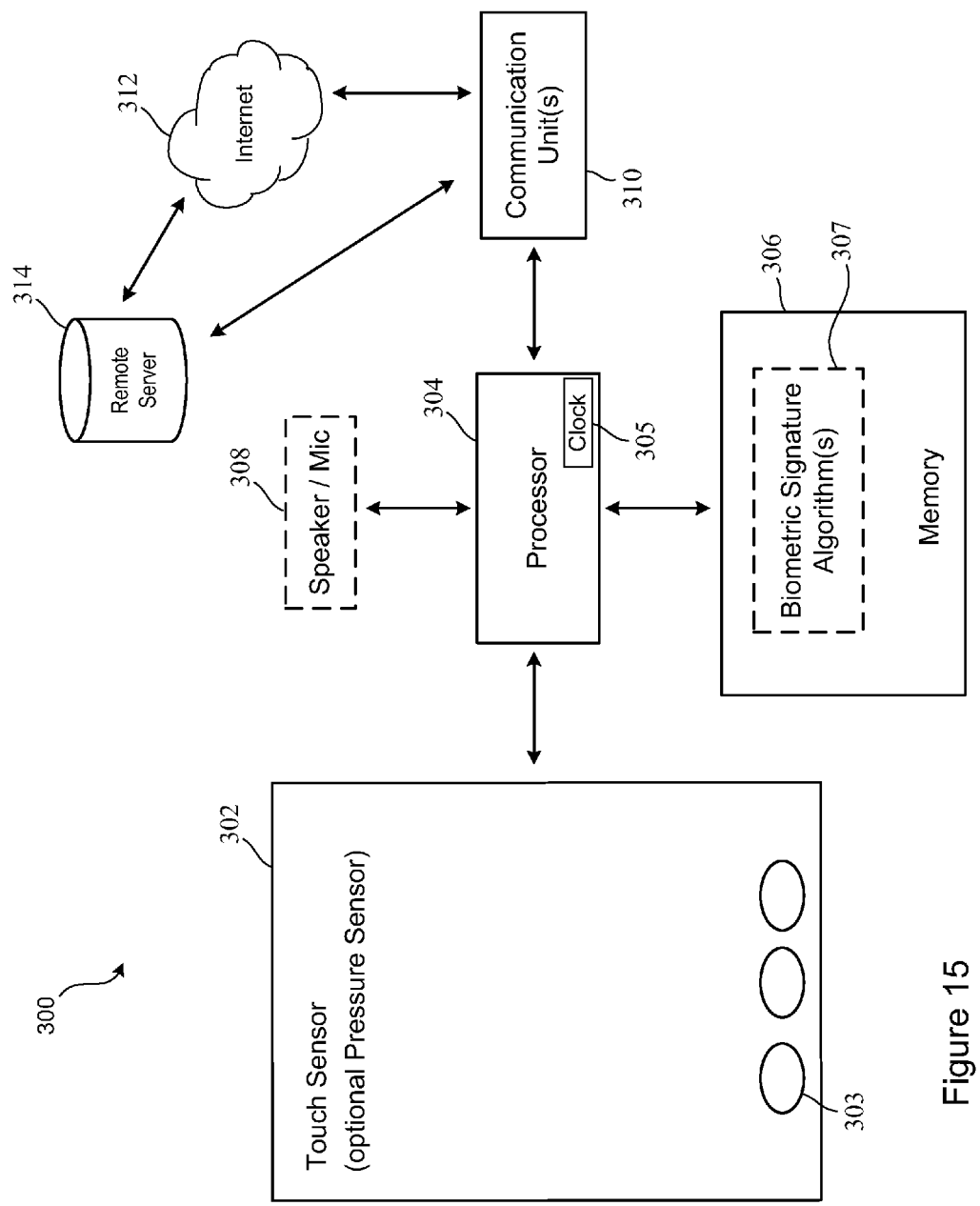
FIG. 15 is a block diagram of a system which includes an electronic device configured to implement a biometric system and method according to various embodiments of the disclosure.

FIG. 15 is a block diagram of a system 300 which includes an electronic device configured to implement a biometric system and method according to various embodiments of the disclosure. The system 300 shown in FIG. 15 includes a touch sensor 302 coupled to a processor 304. The touch sensor 302 may include one or more user-actuatable buttons 303. The touch sensor may be fabricated according to various technologies, including capacitive, resistive, force, and acoustic technologies, for example. The touch sensor 302 may optionally incorporate an integral or separate pressure sensor capable of sensing pressure at various locations of the sensor surface. The processor 304 includes a clock 305 which may be separate from the main clocks of the processor 304. The clock 305 may be dedicated to perform clocking functions for the biometric signature algorithms 307 stored in a memory 306 coupled to the processor 304. A speaker and/or microphone unit 308 may be included.

The system 300 may further include one or more wired and/or wireless communication units 310, such as one or more radios (e.g., cellular, Wi-Fi), transceivers (e.g., Bluetooth), and hardwire interfaces (e.g., Ethernet). The communication unit(s) 310 are coupled to the processor 304 and provide communicate coupling to external systems and networks, such as the Internet 312. The processor 304 may communicate with a remote server 314, for example, via the Internet 312 or other communication link. As discussed previously, biometric data can be transferred between the processor 304/memory 306 and the remote server 314. The processor 304 and the remote server 314 may operate cooperatively during one or more biometric processes described hereinabove. Components of the system 300 shown in FIG. 15 can be incorporated in a variety of electronic devices, such as a mobile phone, tablet, PC, and the like.

The foregoing description of the example embodiments has been presented for the purposes of illustration and description. It is not intended to be exhaustive or to limit the inventive concepts to the precise form disclosed. Many modifications and variations are possible in light of the above teaching. Any or all features of the disclosed embodiments can be applied individually or in any combination are not meant to be limiting, but purely illustrative. It is intended that the scope be limited not with this detailed description, but rather determined by the claims appended hereto.

What is claimed is:

1. A processor-implemented method, comprising:
sensing a contact event occurring between a body part of a user and a touch sensor;
storing in a memory, for the contact event, a sequence of data frames, each of the data frames comprising a three-dimensional data set comprising two-dimensional contact data and a time-dependent reference associated with a contact pattern that evolves over time during contact between different portions of the user's body part and the touch sensor;
measuring pressure exerted at different locations of the touch sensor by the user's body part during the contact event; and
generating, by a processor, biometric signature data using the three-dimensional data sets of the sequence of data frames and the measured pressure.

2. The method of claim 1, wherein each of the data frames comprises spatial dimensions corresponding to the geometry of a portion of the user's body part.

3. The method of claim 1, wherein the sequence of data frames comprises a sequence of geometric images for the contact event.

4. The method of claim 1, wherein each of the data frames comprises:
an involuntary spatial component associated with a contact pattern that evolves during the contact event; and
an involuntary time component associated with the manner in which the contact pattern changes over time during the contact event.

5. The method of claim 1, wherein each frame of data is captured in response to a triggering event based on development of the contact pattern.

6. The method of claim 1, wherein each frame of data is captured in response to a triggering event based on development of the contact pattern, the triggering event comprising exceeding a predetermined total mass count threshold, the total mass count corresponding to an area of the touch screen covered by a portion of the body part at a particular time.

7. The method of claim 1, wherein each frame of data is captured in response to a triggering event based on development of the contact pattern, the triggering event comprising filling of a designated segment of the touch sensor to a predetermined level.

8. The method of claim 1, wherein the biometric signature data is generated during an enrollment process, and the method further comprises:
sensing a subsequent contact event occurring between the body part of the user and the same or different touch sensor;
storing, for the subsequent contact event, a sequence of subsequent data frames each comprising contact data associated with a different portion of the user's body part;
generating a contact pattern using the subsequent sequence of data frames; and
validating or invalidating the contact pattern using the biometric signature data.

9. The method of claim 1, further comprising:
prior to performing a user-selected function, verifying the biometric signature data of the user; and
performing the user-selected function only upon successful verification of the biometric signature data.

10. The method of claim 1, wherein the method is performed by a mobile electronic device.

11. An apparatus, comprising:
a touch sensor configured to sense a contact event occurring between a body part of a user and the touch sensor, the touch sensor configured to produce contact data and sense pressure in response to the sensed contact event; and
a processor coupled to the touch sensor and memory, the processor configured to store in the memory a sequence of data frames, each of the data frames comprising a three-dimensional data set comprising two-dimensional contact data and a time-dependent reference associated with a contact pattern that evolves over time during contact between different portions of the user's body part and the touch sensor, the processor also configured to measure pressure exerted at different locations of the touch sensor by the user's body part during the contact event, and the processor further configured to generate biometric signature data using the three-dimensional data sets of the sequence of data frames and the measured pressure.

12. The apparatus of claim 11, wherein each of the data frames comprises spatial dimensions corresponding to the geometry of a portion of the user's body part.

13. The apparatus of claim 11, wherein the sequence of data frames defines a sequence of geometric images for the contact event.

14. The apparatus of claim 11, wherein each of the data frames comprises:
an involuntary spatial component associated with a contact pattern that evolves during the contact event; and
an involuntary time component associated with the manner in which the contact pattern changes over time during the contact event.

15. The apparatus of claim 11, wherein each frame of data is captured in response to a triggering event based on development of the contact pattern.

16. The apparatus of claim 11, wherein each frame of data is captured in response to a triggering event based on development of the contact pattern, the triggering event comprising exceeding a predetermined total mass count threshold, the total mass count corresponding to an area of the touch screen covered by a portion of the body part at a particular time.

17. The apparatus of claim 11, wherein each frame of data is captured in response to a triggering event based on development of the contact pattern, the triggering event comprising filling of a designated segment of the touch sensor to a predetermined level.

18. The apparatus of claim 11, wherein the biometric signature data is generated during an enrollment process, and the processor, exclusive of or in cooperation with an external processor coupled to the apparatus, is configured to:
sense a subsequent contact event occurring between the body part of the user and the same or different touch sensor;
store in the memory, for the subsequent contact event, a sequence of subsequent data frames each comprising contact data associated with a different portion of the user's body part;
generate a contact pattern using the subsequent sequence of data frames; and
validate or invalidate the contact pattern using the biometric signature data.

19. The apparatus of claim 11, wherein the processor, exclusive of or in cooperation with an external processor coupled to the apparatus, is configured to:
verify, prior to performing a user-selected function, the biometric signature data of the user; and perform the user-selected function only upon successful verification of the biometric signature data.

20. The apparatus of claim 11, wherein the apparatus is part of a mobile electronic device.

21. A processor-implemented method, comprising:
sensing a contact event occurring between a body part of a user and a touch sensor;
capturing two-dimensional contact data in response to sensing the contact event;
triggering acquisition of individual data frames of a sequence of data frames in response to triggering events, the triggering events based on the captured contact data;
measuring pressure exerted at different locations of the touch sensor by the user's body part during the contact event;
storing in a memory, for each data frame, a three-dimensional data set comprising two-dimensional contact data and a time-dependent reference; and
generating, by a processor, biometric signature data using the three-dimensional data sets of the sequence of data frames and the measured pressure.

22. The method of claim 1, wherein the biometric signature data comprise a time-dependent pattern of geometry of different portions of the user's body part as the contact pattern evolves over time.

23. The apparatus of claim 11, wherein the biometric signature data comprise a time-dependent pattern of geometry of different portions of the user's body part as the contact pattern evolves over time.

* * * * *